(12) United States Patent
Malik et al.

(10) Patent No.: US 10,883,928 B2
(45) Date of Patent: Jan. 5, 2021

(54) NANOSENSOR FOR THE DETERMINATION OF INSECTICIDE

(71) Applicants: Muhammad Imran Malik, Karachi (PK); Muhammad Raza Shah, Karachi (PK); Sana Rahim, Karachi (PK); Sadia Khalid, Karachi (PK); Muhammad Iqbal Bhanger, Karachi (PK); Muhammad Ismail Vohra, Karachi (PK)

(72) Inventors: Muhammad Imran Malik, Karachi (PK); Muhammad Raza Shah, Karachi (PK); Sana Rahim, Karachi (PK); Sadia Khalid, Karachi (PK); Muhammad Iqbal Bhanger, Karachi (PK); Muhammad Ismail Vohra, Karachi (PK)

( * ) Notice: Subject to any disclaimer, the term of this patent is extended or adjusted under 35 U.S.C. 154(b) by 263 days.

(21) Appl. No.: 15/991,800

(22) Filed: May 29, 2018

(65) Prior Publication Data

US 2019/0369011 A1 Dec. 5, 2019

(51) Int. Cl.
*B22F 9/20* (2006.01)
*G01N 33/18* (2006.01)
*G01N 21/31* (2006.01)
*B22F 1/00* (2006.01)

(52) U.S. Cl.
CPC ......... *G01N 21/314* (2013.01); *B22F 1/0018* (2013.01); *B22F 9/20* (2013.01); *B22F 2304/054* (2013.01); *B22F 2304/056* (2013.01); *G01N 33/18* (2013.01); *G01N 2021/3155* (2013.01)

(58) Field of Classification Search
CPC ................. G01N 21/314; G01N 33/18; G01N 2021/3155; G01N 21/554; G01N 21/78; G01N 2021/258; B22F 1/0018; B22F 9/20; B22F 2304/054; B22F 2304/056
See application file for complete search history.

(56) References Cited

PUBLICATIONS

Rahim, Sana et al., "Polystyrene-block-poly(2-vinylpyridine)-conjugated silvernanoparticles as colorimetric sensor for quantitative determination ofCartap in aqueous media and blood plasma," Dec. 22, 2017, Sensors and Actuators B: Chemical, p. 878-887, DOI: 10.1016/j.snb.2017.12.138 (Year: 2017).*

* cited by examiner

*Primary Examiner* — Jennifer Wecker
*Assistant Examiner* — Michael Paul Shimek
(74) *Attorney, Agent, or Firm* — Sarfaraz K. Niazi

(57) ABSTRACT

This invention demonstrates that silver nanoparticles can be synthesized by reducing silver nitrate with sodium borohydride in a presence of surface stabilizer polystyrene-block-poly(2-vinyl pyridine) in order to overcome the aggregation of silver nanoparticles.

6 Claims, 22 Drawing Sheets

Cartap

Deltamethrin

Alpha cypermethrin

Chlorfenapyr

Carbofuran

Clodinafop propargyl

Lambda cyhlalothrin

Diuron

Imida choprid

Lufenron

NANOSENSOR FOR THE DETERMINATION OF INSECTICIDE

BACKGROUND OF THE INVENTION

Use of insecticides in agriculture and other related fields is increasing significantly. After intended application, many recalcitrant and non-biodegradable insecticides survive in the environment for prolonged periods of time. Recently, the presence of insecticides beyond their acceptable limits in surface water was noticed in different cities of the world. These insecticides not only influence the aquatic life but also have adverse effects on human beings. Hence, development of simple, effective, and inexpensive analysis procedures are imperative for specific and quantitative detection of insecticides in water. Several different techniques such as chromatography, electroanalysis, photoluminescence and fluorescence have been employed for this purpose. However, these techniques require expensive instrumentation, long analysis time, complicated procedures and trained technicians. The above-mentioned factors are major barriers in the development of rapid, on-site and routine screening procedures.

Remarkable optical properties of metallic NPs due to collective oscillation of surface electrons in a conduction band after interaction with electromagnetic radiation (EMR) make them an excellent candidate for application as nanosensors. The optical response of NPs depends upon size, shape and interparticle distances. Particularly, silver and gold NPs have gained extensive consideration in recent years. These NPs show surface plasmon resonance (SPR) band in visible region (380-750 nm). During the recognition process, the surrounding environment of NPs changes due to analyte interaction with different groups on the surface of NPs that causes a shift in surface plasmon band.

Cartap, S,S-[2-(dimethylamino)-1,3-propanediyl] dicarbamothioate, a thiocarbamate, is a precursor or analogue of natural insecticide neurotoxin that directly attacks nervous system of insects, included in group 14 of IRAC MoA classification. It is one of the most widely used insecticides for rice and sugarcane crops. Cartap was considered non-toxic earlier however, recent cases of cartap poisoning have prompted development of specific methods for its detection and quantification. Headache, palpitation, flushed face, irritation of the nose, throat, eyes and skin are the initial indications of cartap effects to humans.

Secondary interactions such as hydrogen bonding, van der waals forces, π-π stacking, host-guest mechanism, charge transfer, electrostatic attraction and antigen-antibody interactions play a vital role in chemosensing. In this context, various natural macromolecules such as proteins, flavonoids, liposomes and polysaccharides as well as synthetic macromolecules such as polymers have been employed for construction of nanosensors. Metal nanoparticles stabilized through nitrogen containing compounds allows for creation of positive charges on the surface of the compound due to donation of electron pairs by nitrogen that render their utilization for detection of anions. Homo and block copolymers of poly(2-vinyl pyridine) (P2VP) can be potential source of basic nitrogens to chelate metal nanoparticles through electrostatic interaction. P2VP has a very low contact angle with Au (9°), and 20 nm AuNPs stabilized at a PS-P2VP interface tend to diffuse into P2VP. Successful utilization of P2VP homopolymers for stabilization of AuNPs has been shown in our recent publication. Precise control of the particle location within P2VP domain of P(S-VP) block copolymer stabilized AuNPs has been demonstrated. The stabilization of AuNPs by 4-(dimethylamino) pyridine is also reported.

Herein, we report a new and facile one-pot robust approach for synthesis of thermally stable P(S-VP)-conjugated silver nanoparticles (AgNPs). P(S-VP)-AgNPs are synthesized by reduction of silver nitrate in presence of sodium borohydride with P(S-VP). Specifically, we demonstrate the utilization of chelating ability of pyridine moiety of polymer for stabilization of AgNPs. The synthesized AgNPs were characterized by UV-visible spectroscopy, zetasizer, FTIR and AFM. Further, the P(S-VP)-AgNPs were utilized for selective detection and quantification of cartap in presence of other interfering species and in real samples such as ground water and blood plasma. The proposed procedure offers fast, economical and sensitive method for detection of cartap in water and physiological fluids for routine analysis.

BRIEF SUMMARY OF THE INVENTION

The first aspect of the present invention provides a method of preparation of silver nanoparticles by using a polystyrene-block-poly(2-vinyl pyridine) as a stabilizing agent, the method comprising the steps of: (a) stabilizing the ratio at which the silver nanoparticles are stable by measuring the absorbance of silver nanoparticles at 400-450 nm, (b) quantifying the silver nanoparticles by determining the size, surface charge, and size distribution of silver nanoparticles through atomic force microscopy and zetasizer, (c) determining the stability of silver nanoparticles as a function of time, temperature, electrolyte concentration and pH, by measuring the absorbance at a wavelength of 400-450 nm.

The second aspect of the present invention is to provide a method of detecting cartap, a thiocarbamate insecticide. The method is comprised of following steps: (a) adding insecticide cartap and other insecticides including deltamethrin, Alpha-cypermethrin, carbofuran, chlorfenapyr, Lambda-cyhlalothrin, diuron, imidacloprid, lufenron and clodinafop propargyl, to silver nanopartciles to determine the interactions of silver nanoparticles with insecticides, (b) measuring change in position of the absorption spectrum, which results from the interactions of silver nanoparticles with insecticide.

The third aspect of the present invention provides a method of quantifying an insecticide cartap, a thiocarbamate insecticide, in spiked tap water, surface runoff water and human blood plasma. The method comprised of following steps: (a) adding spiked tap water/surface runoff water/human blood plasma to silver nanopartciles to determine the interactions of silver nanoparticles with insecticide, (b) measuring change in position of the absorption spectrum, which results from the interactions of silver nanoparticles with cartap.

DETAILED DESCRIPTION OF THE INVENTION

This invention presents a sensitive colorimetric sensor for cartap, a thiocarbamate insecticide. When an insecticide cartap is treated with the P(S-VP)-AgNPs, the insecticide interacts electrostatically with P(S-VP)-AgNPs and reduce the size of P(S-VP)-AgNPs so that a change will appear even in the low concentration of the insecticide cartap, making it possible to detect even ppm levels of the insecticide.

In addition, the inventors have paid attention to the property of P(S-VP)-AgNPs that show a minute optical change according to the size of the particles, and have made extensive efforts to enable a low concentration of an insecticide, cartap to be detected in a rapid and facile manner. As a result, the inventors have found that, when an insecticide cartap is added to a solution containing P(S-VP)-AgNPs, the size of P(S-VP)-AgNPs will reduce after interaction with cartap so that the absorption spectrum of the P(S-VP)-AgNPs will change rapidly to enable the presence of the insecticide to be easily recognized, thereby completing the present invention.

Figure 1:
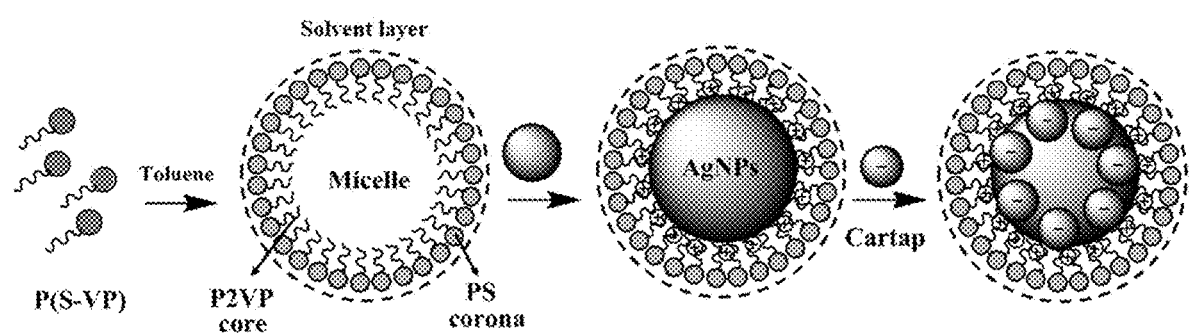
FIG. 1 depicts a schematic representation of cartap recognition of P(S-VP)-AgNPs through electrostatic interactions
Figure 2:
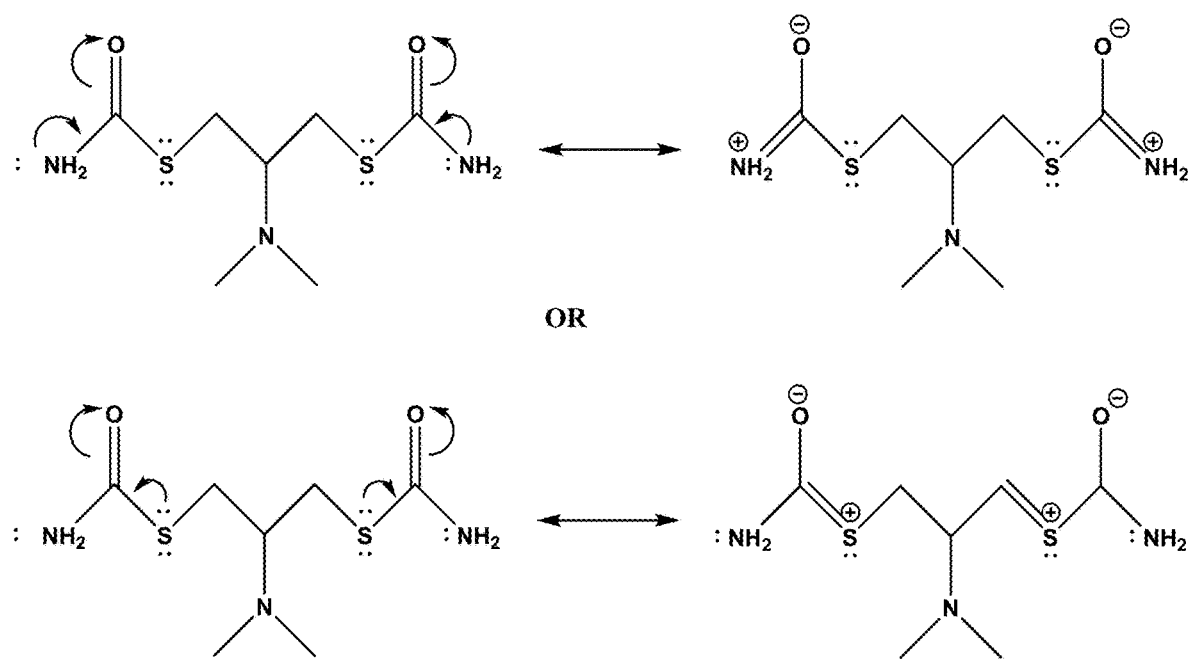
FIG. 2 depicts a resonating structure of Cartap

In embodiments of this invention, a simple method of silver nanoparticles based nanosensor using polystyrene-block-poly(2-vinylpyridine) P(S-VP) block copolymer as stabilizing agent was developed. P(S-VP) tends to make micelles in toluene that is good solvent for PS while non-solvent for P2VP. PS block makes the corona while P2VP tend to be away from toluene making core of the micelles. AgNPs formed inside the core consisting P2VP results positive surface charges on the surface of polymer because nitrogen in the P2VP block donated their lone pair of electrons to silver metal. Cartap has negative charges on its surface due to resonance in the molecule, FIG. 2. When this negatively charged insecticide cartap is added in P(S-VP)-AgNPs solution, it is attracted towards positive charges on the P2VP block because of its resonating structure, FIG. 1. The resonating structure of cartap is depicted in FIG. 2.

This invention demonstrates that silver nanoparticles can be synthesized by reducing silver nitrate with sodium borohydride in a presence of surface stabilizer polystyrene-block-poly(2-vinyl pyridine) in order to overcome the aggregation of silver nanoparticles. Processes of preparing silver nanoparticles in a liquid state include a process of reducing a metal salt at room temperature using polystyrene-block-poly(2-vinyl pyridine) as stabilizing agent and the process of determining the stability of silver nanoparticles as a function of time, electrolyte and pH at room temperature. For determining the stability of silver nanoparticles as a function of temperature, the solution of silver nanoparticles are heated at boiling temperature of solvent used in synthesis of silver nanoparticles.

Silver nanoparticles are widely used in chemical and biochemical sensing. Silver nanoparticles have a characteristics UV-vis spectrum. Silver nanoparticles have a characteristic color under visible light; the color is very much dependent upon the constituents of the surroundings. Any specie present in a sample that interact with silver nanoparticles causes a change in size of the silver nanoparticles, and as a result, the local surface plasmon conditions changes, and thus the color of the silver nanoparticles solution changes under visible light. In other words, the blue shift occurs while the distance between the nanoparticles becomes larger, and the original yellow color of the nanoparticles changes to slightly brownish yellow with the progress of reaction between the silver nanoparticles and sample.

The inventors have attempted to develop a colorimetric sensor enabling a sample to be visibly measured based on the color change of a solution itself, which occurs when there is a specific reaction between an insecticide cartap and silver nanoparticles, without using a particular analysis system.

Silver nanoparticles are characterized by the strongest peak at 428 nm in UV-vis spectrum. However, it has been found by measurement with a UV-vis spectrophotometer that silver nanoparticles are reduced in size as a result of a reaction between insecticide and silver nanoparticles and the absorption spectrum thereof changes so as to have the new peak at a wavelength of 410 nm.

Thus, one aspect of the present invention provides a method of preparation of silver nanoparticles by using a polystyrene-block-poly(2-vinyl pyridine) as stabilizing agent. The method comprising the steps of: (a) stabilizing the ratio at which the silver nanoparticles are stable by measuring the absorbance of silver nanoparticles, which results at a wavelength of 400-450 nm, (b) quantifying the silver nanoparticles by determining the size, surface charge, and size distribution of silver nanoparticles through atomic force microscopy and zetasizer, (c) determining the stability of silver nanoparticles as a function of time, temperature, electrolyte concentration and pH, by measuring the absorbance at a wavelength of 190-800 nm.

In the process, metal nanoparticles are prepared by mixing a metal salt solution with a solution of polystyrene-block-poly(2-vinyl pyridine) in a solvent, and then adding a strong reducing agent such as sodium borohydride at a room temperature under stirring.

A change in the absorption spectrum of P(S-VP)-AgNPs was measured using a UV visible spectrophotometer to determine the stability of P(S-VP)-AgNPs at elevated temperature i.e. at the boiling temperature of solvent and at various electrolyte concentrations. As a result, the enhancement in absorption intensity of maxima ($A_{max}$) occurred in temperature treated sample that suggests that temperature treated P(S-VP)-AgNPs are relatively more stable, might be due to better conversion of silver ions into silver nanoparticles or increased solubility of high molar mass polymer. Furthermore, P(S-VP)-AgNPs were stable over a wide range of concentration of sodium chloride (0.01 mM to 1.0 mM). Aggregation was only observed by addition of sodium chloride solution having concentration beyond 5.0 mM, attributed to the aggregation effect by ions present in solution. P(S-VP)-AgNPs remained stable for more than six months at ambient temperature.

The present invention demonstrates a change in the absorption spectrum of P(S-VP)-AgNPs in UV-visible spectrum after adding insecticides to a P(S-VP)-AgNPs solution. As a result, it could be seen that the reduction of size of P(S-VP)-AgNPs was induced by the cartap to produce a new spectrum showing a peak at 410 nm, suggesting that the cartap can be easily and rapidly detected based on a visible change in the spectrum.

Figure 3:
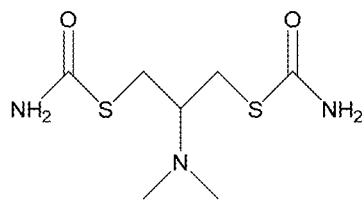
FIG. 3 depicts a structure of cartap and other interfering insecticides
Figure 3:
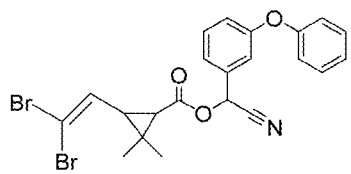
Figure 3:
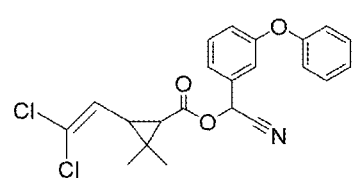
Figure 3:
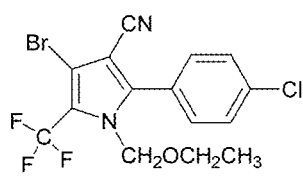
Figure 3:
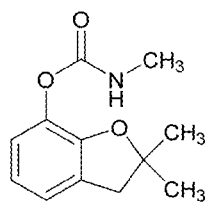
Figure 3:
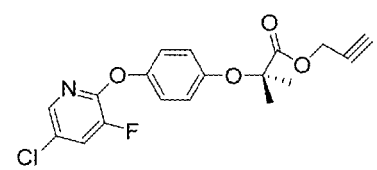
Figure 3:
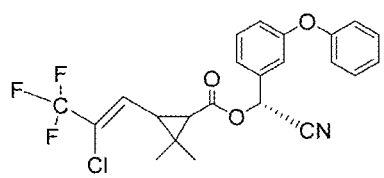
Figure 3:
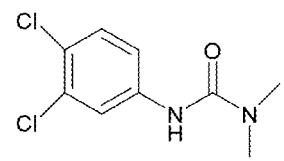
Figure 3:
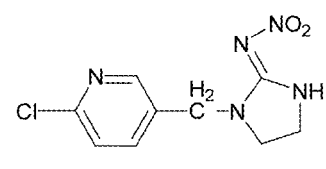
Figure 3:
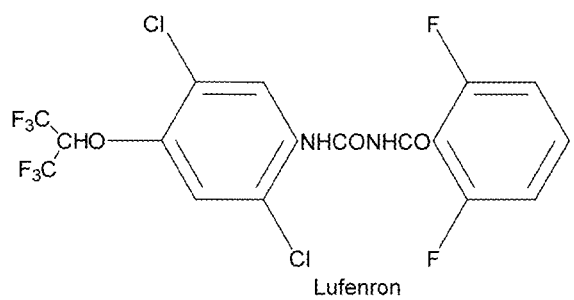

The present invention demonstrates the recognition behavior of P(S-VP)-AgNPs for cartap in presence of various insecticides such as deltamethrin, alpha-cypermethrin, carbofuran, chlorfenapyr, clodinafop propargyl, lambda-cyhlalothrin, diuron, imidacloprid and lufenron. Structures of the competitive insecticides used in this study are depicted in FIG. 3

In embodiments of the present invention, the concentration of the silver nanoparticles is 1 mM. Also, the detection concentration of the insecticide may be 0.036-0.36 $\mu gL^{-1}$, and the optimum pH for the detection of the insecticide cartap may be 8-12, preferably 8-10.

Thus, the second aspect of the present invention also provides a method of detecting cartap, a thiocarbamate insecticide. The method comprising the steps of: (a) adding insecticide cartap and other insecticides including; deltamethrin, Alpha-cypermethrin, carbofuran, chlorfenapyr, Lambda-cyhlalothrin, diuron, imidacloprid, lufenron and clodinafop propargyl, to silver nanopartciles to determine the interactions of silver nanoparticles with insecticides, (b) measuring change in position of the absorption spectrum, which results from the interactions of silver nanoparticles, (c) determining the interference of other non-interacting insecticide during recognition of cartap by P(S-VP)-AgNPs.

In an example of the present invention, it could be seen that, when an insecticide cartap is added in a silver nanoparticle solution, a great difference in absorbance between the concentrations of the insecticide appeared, and the difference was most clear at a wavelength of 410 nm. Thus, a calibration curve as a function of the concentration of the insecticide was plotted using the absorbance values at a wavelength of 410 nm, FIG. 13. The detection limit was 0.06 $\mu gL^{-1}$ and the concentration range is 0.036-0.36 $\mu gL^{-1}$.

In an example of present invention, the results of determining an insecticide cartap using embodiments of the present invention was evaluated in the presence of interfering insecticides. As a result, it could be seen that a characteristic absorption spectrum of a mixture of P(S-VP)-AgNPs and cartap at 410 nm was not influenced by presence of other insecticides.

The present invention demonstrates the utility and efficiency of optimized cartap recognition system. P(S-VP)-AgNPs were employed for cartap recognition in spiked tap water, surface runoff water and human blood plasma. All samples were spiked with 0.1 mM concentration of cartap before analysis. It could be seen that the distinctive cartap recognition signal is observed in P(S-VP)-AgNPs with 0.1 mM cartap spiked tap water. Same comparison for surface runoff water with similar results is presented. However, in case of blood plasma, only a hypochromic shift with a slight blue shift of 4-5 nm band is observed, suggested that the proposed cartap recognition system can be effectively utilized for detection of cartap in water treatment and blood testing.

Thus, the third aspect of the present invention also provides a method of determining an insecticide cartap, a thiocarbamate insecticide, in spiked tap water, surface runoff water and human blood plasma. The method comprising the steps of: (a) adding spiked tap water/surface runoff water/ human blood plasma to silver nanoparticles to determine the interactions of silver nanoparticles with insecticide, (b) measuring change in the absorption spectrum, which results from the interactions of silver nanoparticles.

In an example of present invention, the results of determining an insecticide cartap using embodiments of the present invention was determined in the tap water, surface runoff water and blood plasma. As a result, it could be seen that method of determining a cartap using silver nanoparticles according to embodiments of the present invention is as accurate as other advanced method, suggesting that the method of the embodiments of the present invention is more rapid, efficient and more economical than the other advanced instrumental methods.

EXAMPLES

Materials and Instrumentation

Polystyrene-block-poly(2-vinyl pyridine) $PS_{26K}$-b-$P2VP_{4.8K}$ (PDI=1.15) was purchased from Polymer Source Inc (Quebec, Canada) [referred as P(S-VP) in text]. Silver nitrate ($AgNO_3$) (Sigma Aldrich, USA) was the starting material for the synthesis of silver nanoparticles. $NaBH_4$ (TCI, Tokyo, Japan) was used as reducing agent for $AgNO_3$. HPLC grade methanol and toluene (RCI Labscan limited, Thailand) were used as solvents. All the reagents were used as received. Insecticides samples were collected from Industrial Analytical Centre (IAC), International Centre for Chemical and Biological Sciences (ICCBS), University of Karachi, Pakistan.

Glassware were washed with aqua regia, oven-dried and rinsed with deionized water and methanol prior to use.

A digital pH meter (Oakton, Eutech) model 510, with a Ag/AgCl reference electrode and a glass working electrode was used to adjust pH of P(S-VP)-AgNPs solutions. UV-visible spectra were recorded with a double beam Shimadzu UV-1800 series spectrophotometer operated at a wavelength range of 190-800 nm using quartz cuvette of one centimeter path length. Particle size distribution and zeta potential of P(S-VP)-AgNPs before and after treatment with cartap were determined by zetasizer, Nano-ZSP (Malvern Instruments). The analysis was performed at a scattering angle of 90° using disposable cuvette for zetasizer and dip cell cuvette for zeta potential studies, at 25° C.

FTIR spectra were recorded on a Bruker Vector 22 spectrometer in mid IR range (400-4000 $cm^{-1}$) using KBr pellet. Ten scans were used to attain the spectral resolution of 0.1 $cm^{-1}$.

P(S-VP)-AgNPs topographical images were recorded by Agilent 5500 atomic force microscope (AFM), (Arizona, USA). Triangular soft silicon nitride cantilever (Veeco, model MLCT-AUHW) with a nominal value of 0.01 $Nm^{-1}$ and a spring constant value of 0.1 $Nm^{-1}$ in the tapping mode was used for all measurements. A drop of freshly prepared sample was taken on the surface of silicon wafer, and subsequently dried in air before analysis.

Example 1

Synthesis of P(S-VP)-AgNPs Using P(S-VP)

For polystyrene-block-poly(2-vinyl pyridine) (P(S-VP)-AgNPs) solution, 0.154 g of polymer was dissolved in 50 mL of toluene to make a concentration of 0.1 mM. For silver solution, 0.0422 g of silver nitrate salt was dissolved in 50 mL of methanol/toluene (10:90) mixture to make a concentration of 5 mM. The solution of silver nitrate was then diluted with methanol to a concentration of 1.0 mM for preparation of sample.

Figure 4:
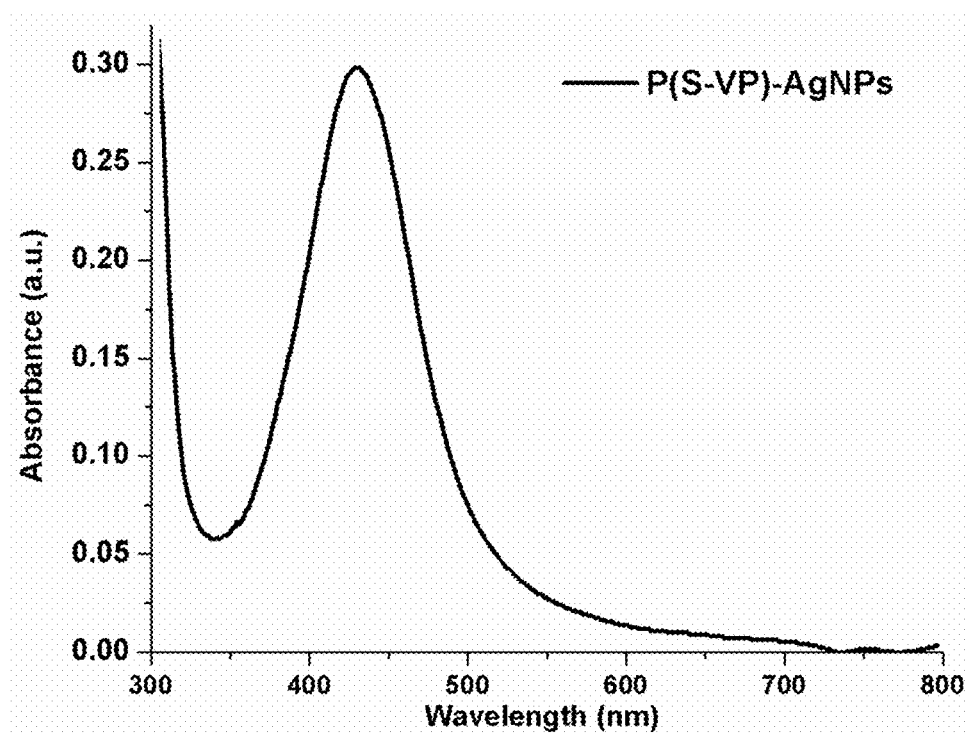
FIG. 4 depicts an UV-visible spectrum of P(S-VP)-conjugated AgNPs.

For the synthesis of polystyrene-block-poly(2-vinyl pyridine)-conjugated silver nanoparticles, 1.0 mL of 0.1 mM P(S-VP) in toluene was mixed with 30 mL of 1.0 mM $AgNO_3$ in methanol/toluene (10:90) mixture. 0.1 mL of 4.0 mM $NaBH_4$ was added into the stirred reaction mixture after 15 min and the mixture was further stirred for 30 min. The color of reaction mixture rapidly changed from colorless to yellow and showed a characteristic absorption spectrum of silver nanoparticles showing absorption at 428 nm, FIG. 4.

1.1. Determination of Amount of P(S-VP) Used in Conjugation with Silver Nanoparticles For determination of amount of conjugated P(S-VP) with AgNPs in reaction mixture, 100 mL of P(S-VP)-AgNPs was centrifuged at 30° C. for 30 min at 14000 rpm. The P(S-VP)-AgNPs settles down at the bottom. The supernatant containing unconjugated P(S-VP) was freeze dried and weighed. The calculated amount of P(S-VP) was subtracted from the initial amount of polymer used in the reaction mixture. Hence, it is concluded that the conjugated P(S-VP) with AgNPs contained about 80 weight % of initial amount of P(S-VP).

Example 2

Figure 5:
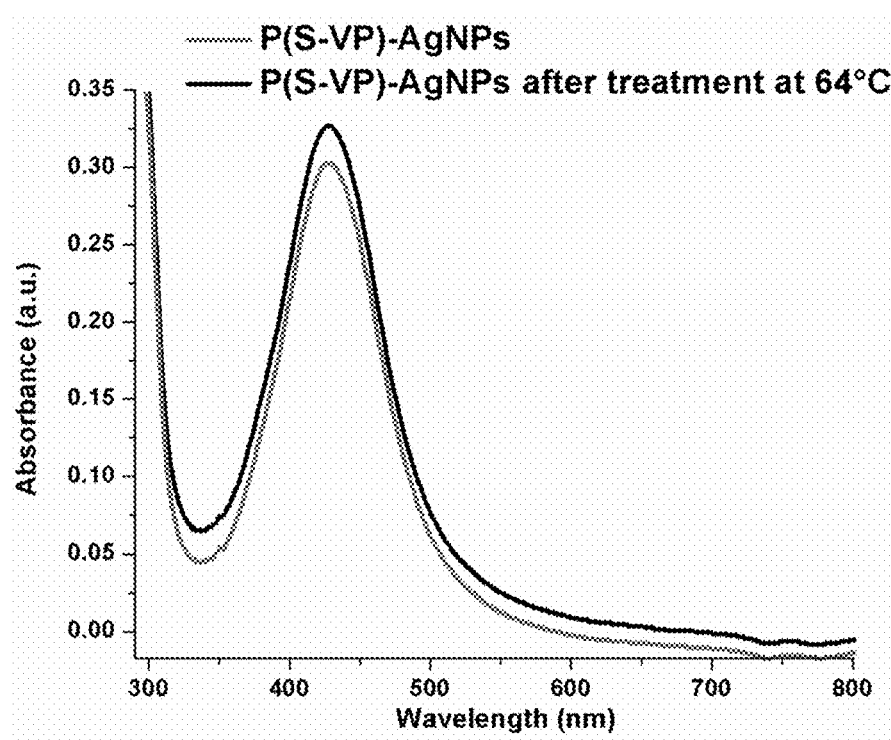
FIG. 5 depicts an UV-visible spectrum of P(S-VP)-conjugated AgNPs after incubation of P(S-VP)-conjugated AgNPs at 64° C. for 10 minutes (B.P. of methanol).

Measurement of Absorbance for P(S-VP)-AgNPs after High Temperature Treatment 2.0 mL solution of P(S-VP)-AgNPs was treated at a temperature of 64° C. i.e., boiling temperature of methanol in a closed container. The reaction mixture was cooled to ambient temperature without any external cooling source and change in the absorption spectrum of treated and untreated samples were measured with a spectrophotometer (FIG. 5). The intensity of the peak in the absorption spectrum was enhanced by temperature treatment without any change in the position of the peak.

Example 3

Change in Absorbance Behavior as a Function of Electrolyte Concentration in P(S-VP)-AgNPs The stock solution of NaCl was prepared by dissolving 14.6250 g of NaCl in 50 mL of 90% methanol to make a concentration of 5M. Further concentrations were made by dilution of 5M NaCl solution to the concentrations of 1M, 500 mM, 100 mM, 50 mM, 1 mM, 0.5 mM, 0.05 mM, and 0.01 mM.

Figure 6:
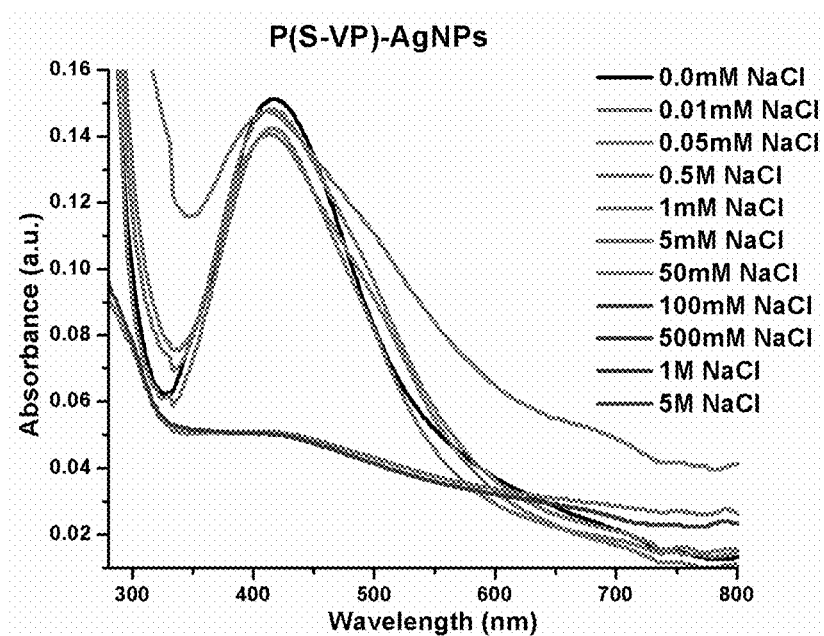
FIG. 6 depicts an electrolyte effect on P(S-VP)-conjugated AgNPs with various salt concentrations (0.01 mM-5M).

A solution of prepared P(S-VP)-AgNPs and salt solutions of varying concentrations were mixed in equal volume ratios, and the mixture was allowed to react at room temperature. Thereafter, the absorption spectrum of the mixture was measured. The results of effect of varying electrolyte concentration are depicted in FIG. 6. The intensity of the absorption spectrum of P(S-VP)-AgNPs decreased gradually with increase in the NaCl concentration in the range of 0.01 mM to 5M.

Example 4

Determination of Change in Particle Size of P(S-VP)-AgNPs after Adding Cartap by Zetasizer The stock solution of cartap, a thiocarbamate insecticide, was prepared by dissolving 0.01187 g of the insecticide in 50 mL of methanol to a concentration of 1.0 mM. The solution was further diluted with methanol to a concentration of 0.1 mM for sample preparation.

Figure 7A:
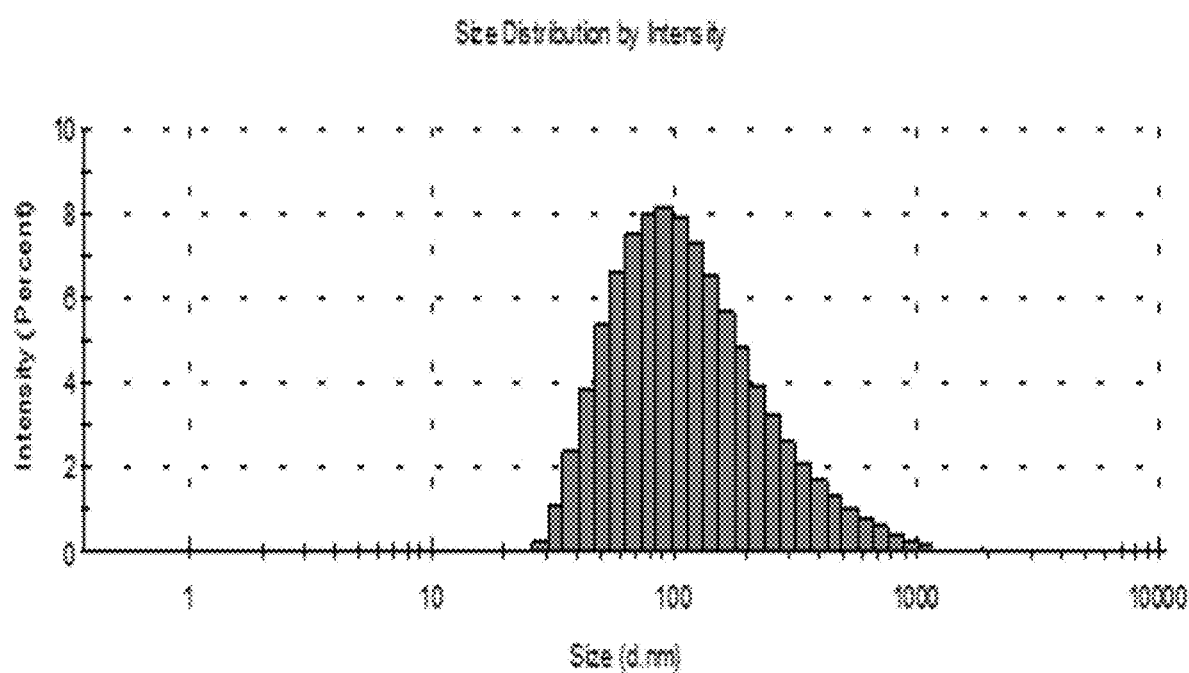
FIG. 7A depicts the size distribution by intensity of P(S-VP)-AgNPs avg size: 104.2±0.68 nm, PDI: 0.22.
Figure 7B:
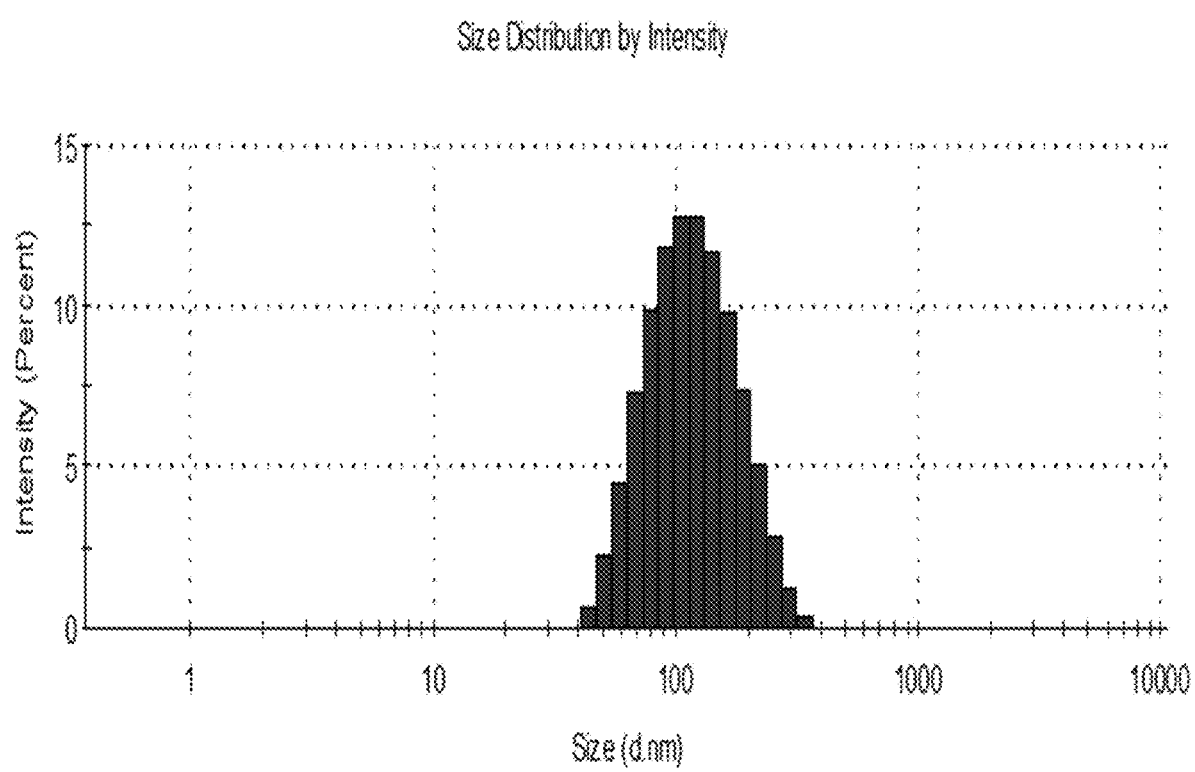
FIG. 7B depicts the size distribution by intensity of P(S-VP)-AgNPs/cartap. avg. size: 89.68±0.57 nm, PDI: 0.08.

A solution obtained by diluting the thiocarbamate insecticide cartap to a concentration of 0.1 mM and P(S-VP)-AgNPs were mixed in equal volume ratios and the change in the size of the P(S-VP)-AgNPs after addition of cartap solution was measured with a zetasizer, FIG. 7. The size of the P(S-VP)-AgNPs was 104.2±0.68 nm that is reduced to 89.68±0.57 nm after addition of cartap. Polydispersity indices of P(S-VP)-AgNPs and P(S-VP)-AgNPs-Cartap were found to be 0.22 and 0.08, respectively. The results suggest that addition of cartap resulted in regularity in the shape and reduction in size of the NPs that can be attributed to the balancing of the surface charges.

Example 5

Figure 8A:
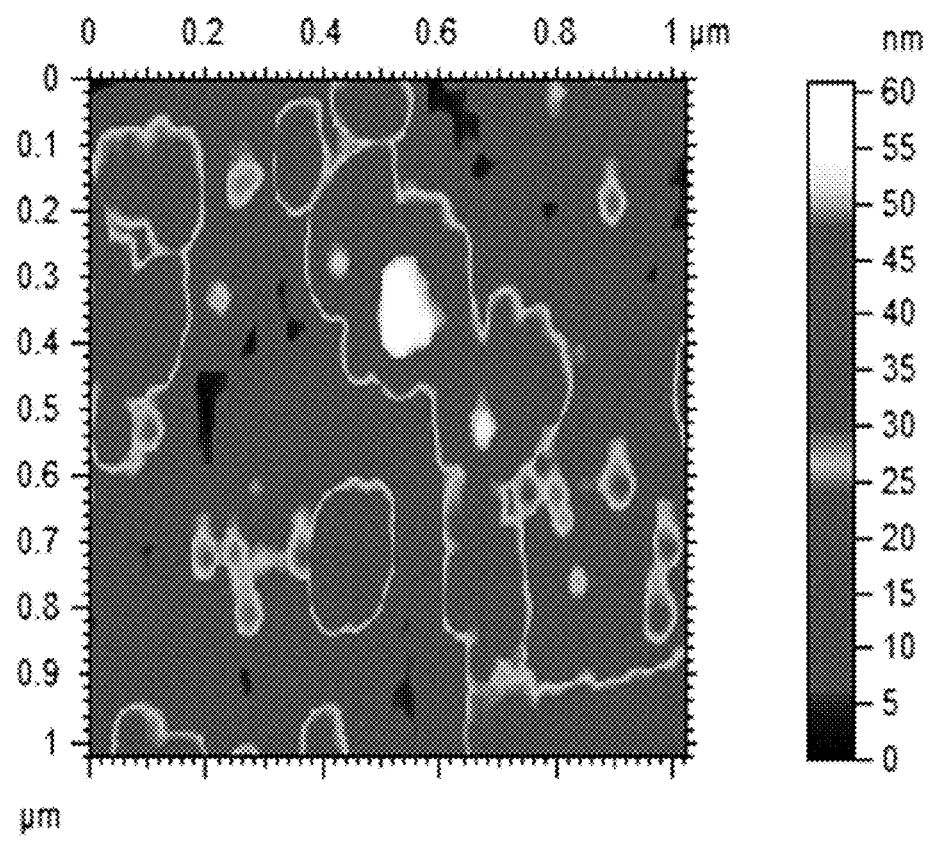
FIG. 8A depicts an atomic force micrographs (AFMs) of P(S-VP)-AgNPs (80-120 nm).
Figure 8B:
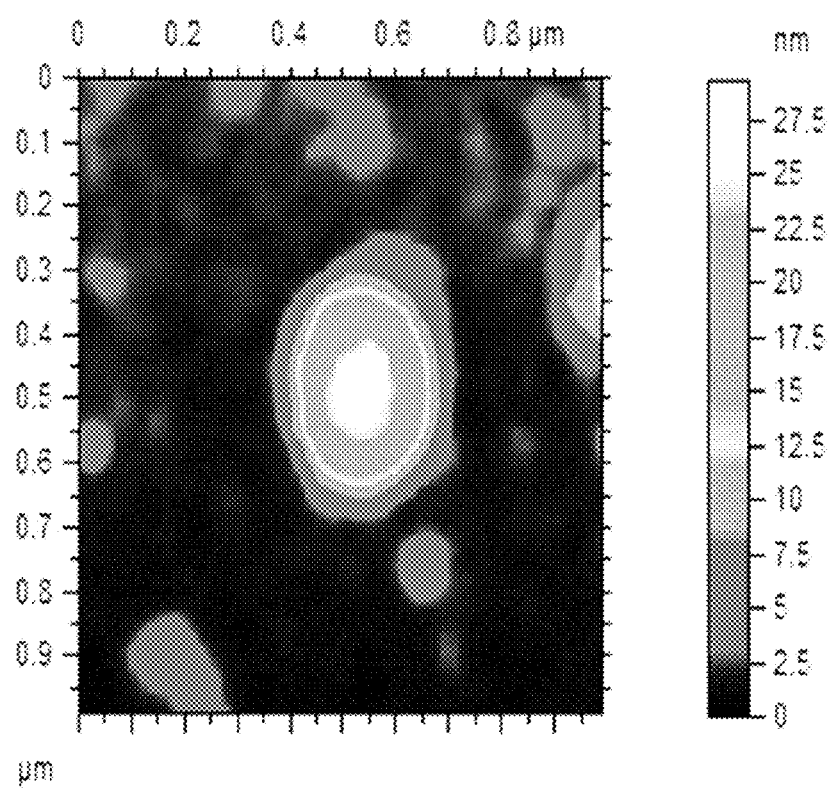
FIG. 8B depicts an atomic force micrograph of P(S-VP)-AgNPs/cartap (60-90 nm).

Determination of Change in Morphology and Particle Size of P(S-VP)-AgNPs by Atomic Force Microscopy Solutions of cartap and P(S-VP)-AgNPs were mixed in the same concentrations and mixing ratios as described in Example 4. The size of the P(S-VP)-AgNPs and P(S-VP)-AgNPs/cartap were measured by atomic force microscopy. The P(S-VP)-AgNPs exhibited an irregular assemblage shape with size of 80-120 nm, FIG. 8A. After addition of cartap, the P(S-VP)-AgNPs/cartap attained a regular shape, and size apparently decreased to 60-90 nm, FIG. 8B. The results suggest that addition of cartap induced stability and regularity to P(S-VP)-AgNPs that may be attributed to surface charge balance.

Example 6

Change in Zeta Potential of Mixture of P(S-VP)-AgNPs and Cartap

Figure 9A:
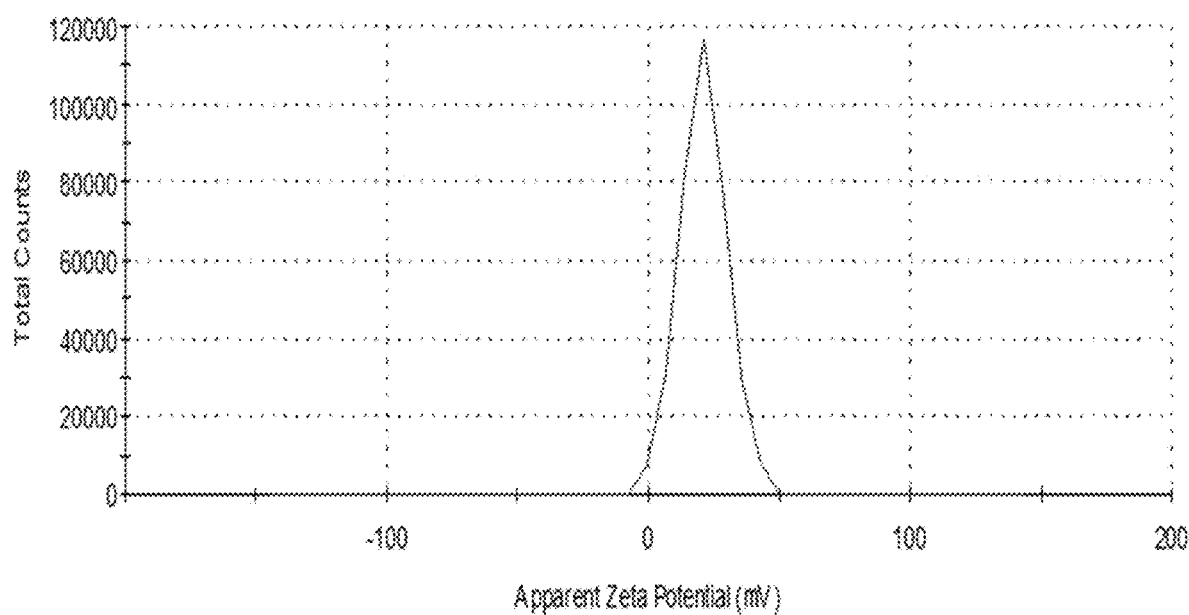
FIG. 9A depicts a Zeta potential distribution of P(S-VP)-AgNPs
Figure 9B:
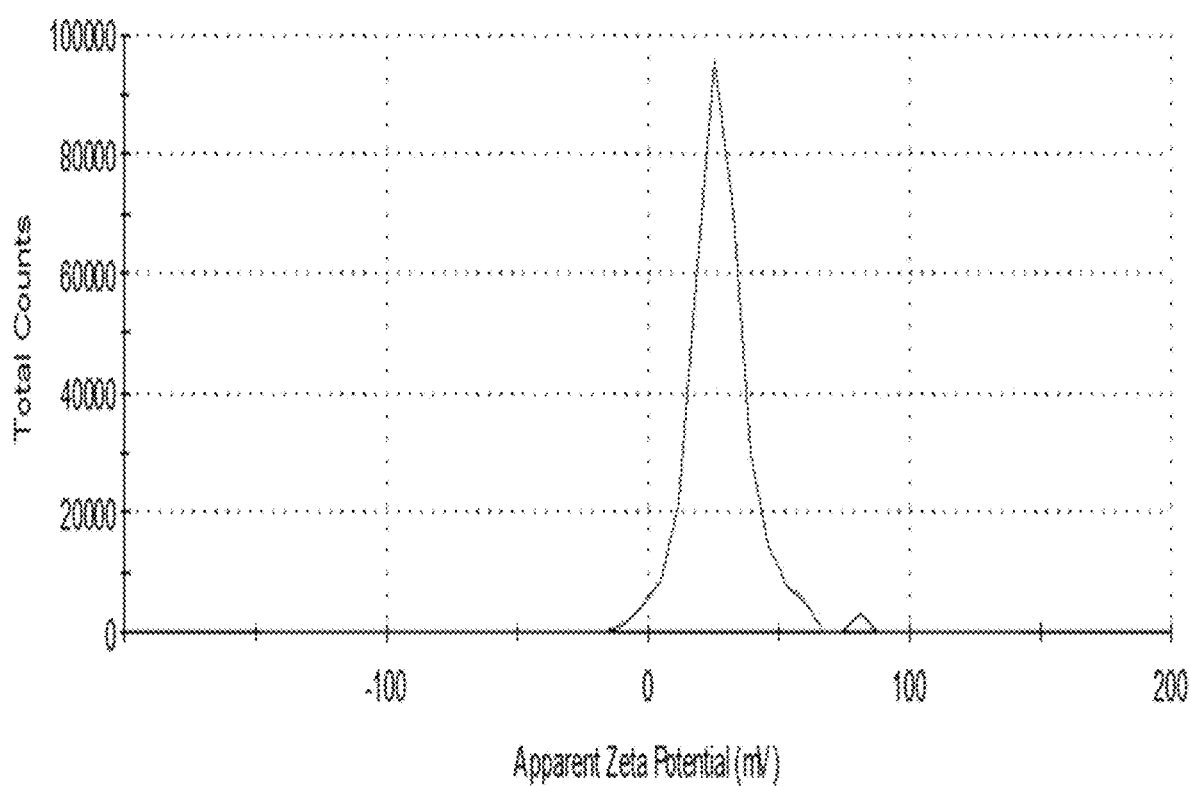
FIG. 9B depicts Zeta potential distribution P(S-VP)-AgNPs/Cartap.

Solutions of cartap and P(S-VP)-AgNPs were mixed in the same concentrations and mixing ratios as described in Example 4. Thereafter, the zeta potential of the P(S-VP)-AgNPs and P(S-VP)-AgNPs was measured with a zetasizer, FIG. 9. The zeta potential of the P(S-VP)-AgNPs was +27.7 mV indicating that the surfaces of P(S-VP)-AgNPs have positive charges. However, cartap addition to the P(S-VP)-AgNPs resulted in reduction of the zeta potential to +20.8 mV. The results suggest that negatively charged insecticide cartap neutralized positive surface charges present on the outer surface P(S-VP)-AgNPs through electrostatic interactions.

Example 7

Figure 10:
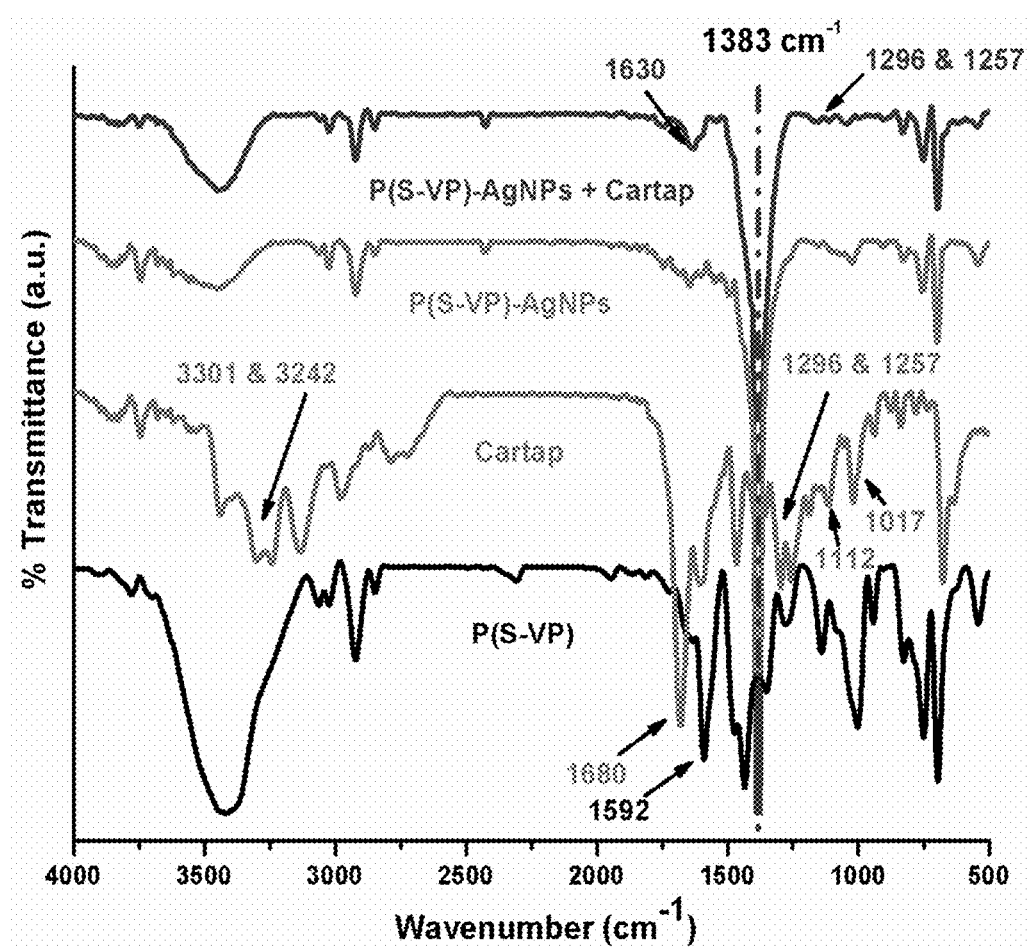
FIG. 10 depicts a FTIR spectra of P(S-VP), Cartap, P(S-VP)-AgNPs, and cartap treated P(S-VP)-AgNPs.

Determination of Nature of Interaction Between P(S-VP)-AgNPs and Insecticide Cartap Through FTIR Solutions of cartap and P(S-VP)-AgNPs were mixed in the same concentrations and mixing ratios as described in Example 4. FTIR studies of P(S-VP), P(S-VP)-AgNPs, and P(S-VP)-AgNPs/cartap were performed to have a deeper understanding of the mechanism of NP formation and recognition of cartap in solution. A comparison between FTIR spectra of P(S-VP), P(S-VP)-AgNPs, and P(S-VP)-AgNPs/cartap suggested that nitrogen atoms in the backbone of polymer stabilized AgNPs, since C=N stretching vibration peak at 1592 $cm^{-1}$ of P(S-VP) disappeared upon the formation of AgNPs, while the rest of the characteristics peaks for P(S-VP) are present (FIG. 10). A new peak appeared at 1383 $cm^{-1}$ that indicates the formation of AgNPs. The FTIR spectra of cartap have C=O stretch at 1680, N—H stretch 3301 and 3242, N—$CH_3$ stretch at 2979, and C—S stretching peaks were observed between 1187 to 1017 $cm^{-1}$. Interestingly, C=O, N—H, N—$CH_3$ and C—S peaks of cartap were absent in a mixture of P(S-VP)-AgNPs/cartap, while the peak at 1383 $cm^{-1}$ was still present and a new peak at 1630 $cm^{-1}$ appeared that indicates the formation of C=N bond. The disappearance of the characteristic cartap peaks indicated the interaction of cartap with polymer instead of silver.

Example 8

Measurement of the Change in Absorption Spectrum Caused by Addition of Cartap and Other Competing Insecticides to P(S-VP)-AgNPs Solutions of cartap/other competing insecticides and P(S-VP)-AgNPs were mixed in the same concentrations and mixing ratios as described in Example 4. The mixture was allowed to react at room temperature. Thereafter, the absorption spectrum of the mixture was measured by UV-Vis spectrophotometer. A rapid change in the position and intensity of the absorption spectrum occurred for cartap compared to no change for other insecticides. Thus, an experiment was performed to examine an element that caused this change.

8.1. Reaction of P(S-VP)-AgNPs and Cartap

A solution obtained by diluting the thiocarbamate insecticide cartap to a concentration of 0.1 mM and P(S-VP)-AgNPs were mixed at a volume ratio of 1:1, and the mixture was allowed to react at room temperature, after which the absorption spectrum of the mixture was measured.

Figure 11:
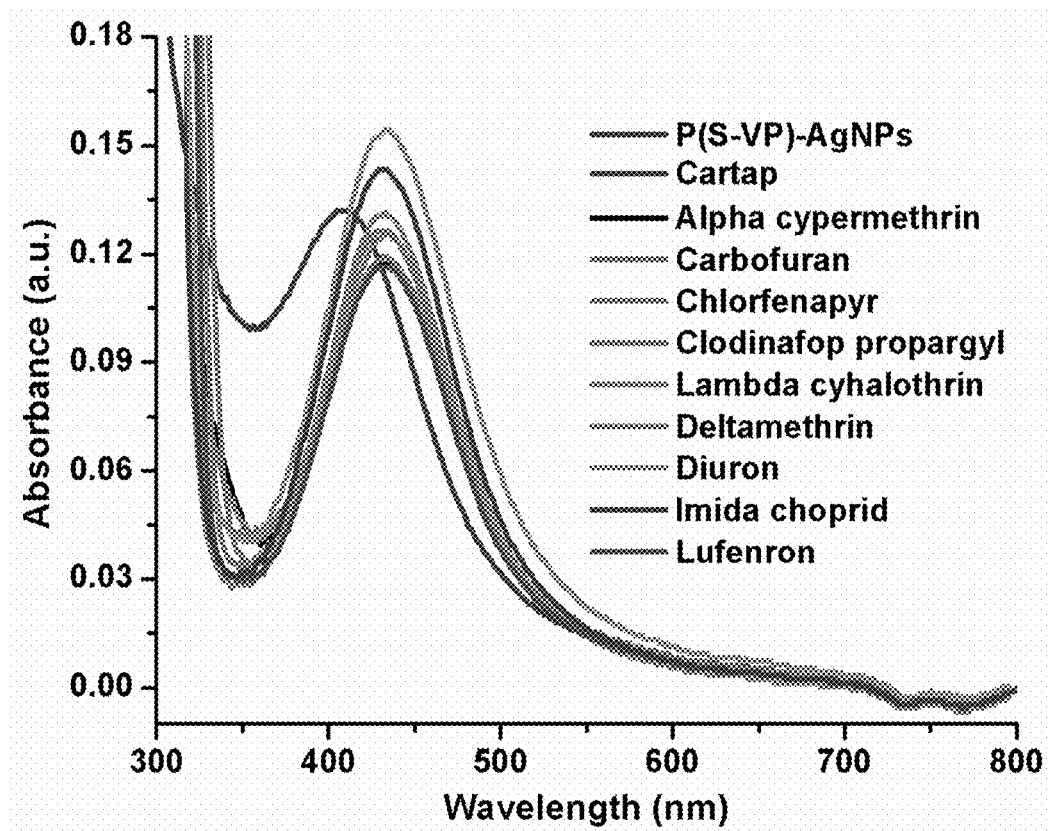
FIG. 11 depicts an UV-visible spectra of P(S-VP)-AgNPs complexed with various insecticides.

Shift of the absorption spectrum to lower wavelength (410 nm) was noticed, FIG. 11. This suggested that the reaction of P(S-VP)-AgNPs with the cartap and thus protecting the silver nanoparticles. This interaction resulted in the shift of the absorption maximum and allowed for detection of thiocarbamate insecticide cartap.

8.2. Reaction of P(S-VP)-AgNPs and Other Insecticides

Same experimental procedure was followed for other insecticides such as deltamethrin, Alpha-cypermethrin, carbofuran, chlorfenapyr, Lambda-cyhlalothrin, diuron, imidacloprid, lufenron and clodinafop propargyl.

No change in the absorption spectrum of P(S-VP)-AgNPs was noticed after addition of other competing insecticides such as deltamethrin, Alpha-cypermethrin, carbofuran, chlorfenapyr, Lambda-cyhlalothrin, diuron, imidacloprid, lufenron and clodinafop propargyl, FIG. 11. Thus, it could be concluded that the proposed colorimetric sensor is very selective and sensitive for cartap in comparison to other competing insecticides.

Example 9

Change in Absorbance of P(S-VP)-AgNPs and P(S-VP)-AgNPs/Cartap at Various pH Values 9.1. Effect of pH on P(S-VP)-AgNPs In order to examine whether the reaction of P(S-VP)-AgNPs with a insecticide is influenced by the pH of the solution, the change in the absorbance at 410 nm with a change in pH was analyzed (the concentration and mixing ratio were the same as described in Example 4).

Figure 12:
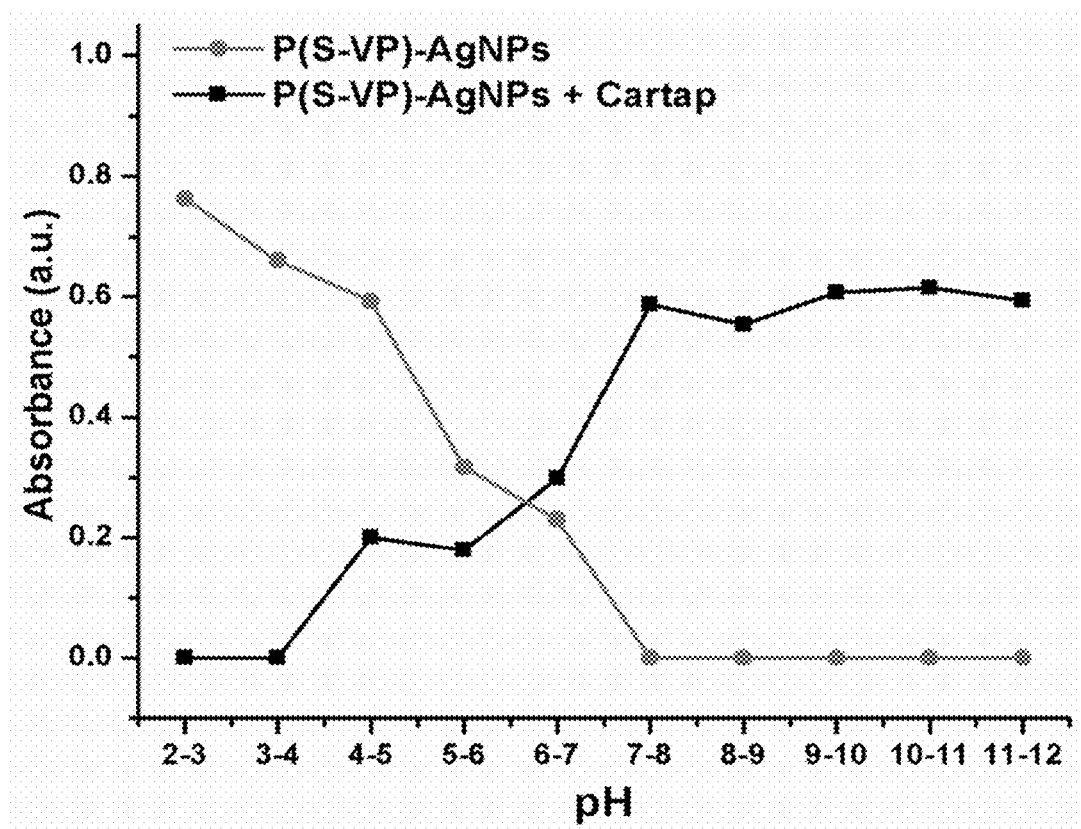
FIG. 12 depicts an effect of pH on accumulation of P(S-VP)-conjugated AgNPs with Cartap.

Absorbance was analyzed at a pH ranging from 2 to 12. The synthesized P(S-VP)-AgNPs were found to be stable in a pH range of 2-7, however, particle agglomeration was noticed above pH 7 that increased with further increase in the pH, suggesting that the P(S-VP)-AgNPs were stable at acidic pH values (FIG. 12).

9.2. Reaction of P(S-VP)-AgNPs and Cartap at Various pH Values

In order to examine whether the reaction of P(S-VP)-AgNPs with a insecticide is influenced by the pH of the solution, the change in the absorbance at 410 nm with a change in pH was analyzed (the concentration and mixing ratio were the same as described in Example 4).

Absorbance was analyzed at a pH ranging from 2 to 12. The synthesized P(S-VP)-AgNPs sensed cartap efficiently in a pH range of 7-12 (FIG. 12). The results suggest that the proposed sensor is very effective for determination of cartap in basic environment.

Example 10

Quantification of Cartap and Construction of Calibration Curve

Figure 13A:
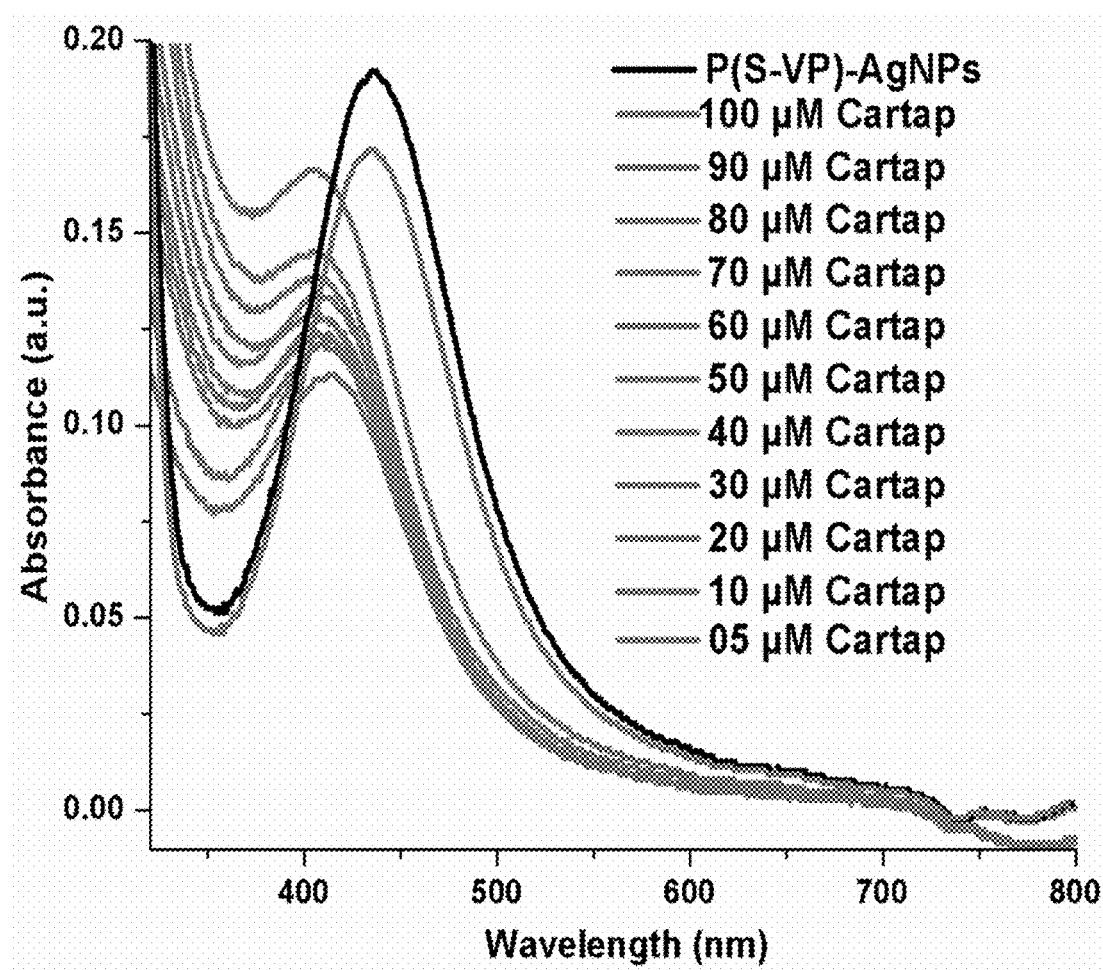
FIG. 13A depicts an UV-visible spectra by using various concentrations of cartap with P(S-VP)-AgNPs.
Figure 13B:
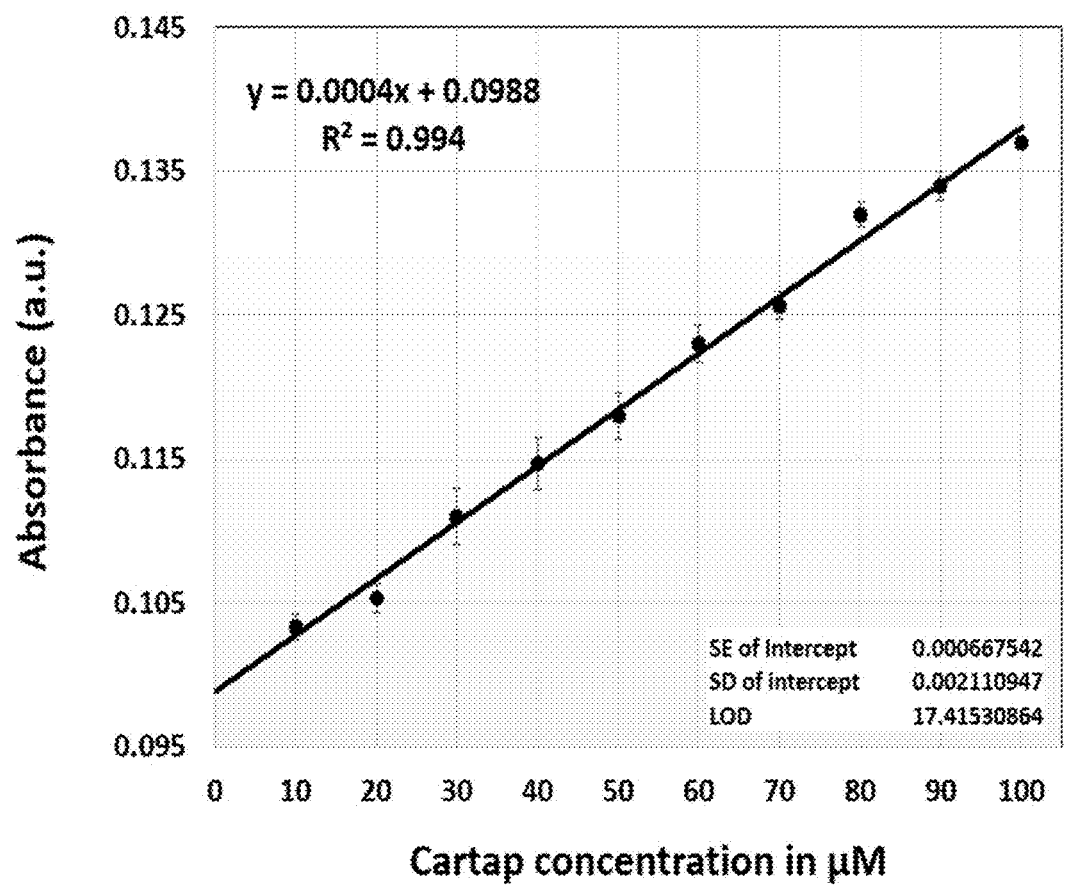
FIG. 13B depicts the calibration curve for amount of cartap at 410 nm.

Samples of cartap solutions having various concentrations ranging from 5 μM to 100 μM were prepared. These cartap solutions of different concentrations and a solution of P(S-VP)-AgNPs were mixed in equal volume ratios, and a change in the absorption spectrum of each mixture was measured with a UV-Vis spectrophotometer (FIG. 13A). As can be seen, the shift of effect of change in concentration can be easily detected by the proposed sensor. Based on the results of the measurement, calibration curve was obtained (FIG. 13B).

Example 11

Limit of Detection

Samples of cartap solutions having various concentrations ranging from 5 μM to 100 μM were prepared. These cartap solutions of different concentrations and a solution of P(S-VP)-AgNPs were mixed in equal volume ratios, and a change in the absorption spectrum of each mixture was measured with a UV-Vis spectrophotometer. The data obtained by measuring change in the absorption spectrum of P(S-VP)-AgNPs by addition of various concentration of cartap revealed that the limit of detection of the proposed sensor is 0.06 pgL$^{-1}$, and the detectable range of the cartap is 0.036-0.36 µgL$^{-1}$.

Example 12

Determination of Binding Stoichiometry of P(S-VP)-AgNPs and Insecticide Cartap

Figure 14:
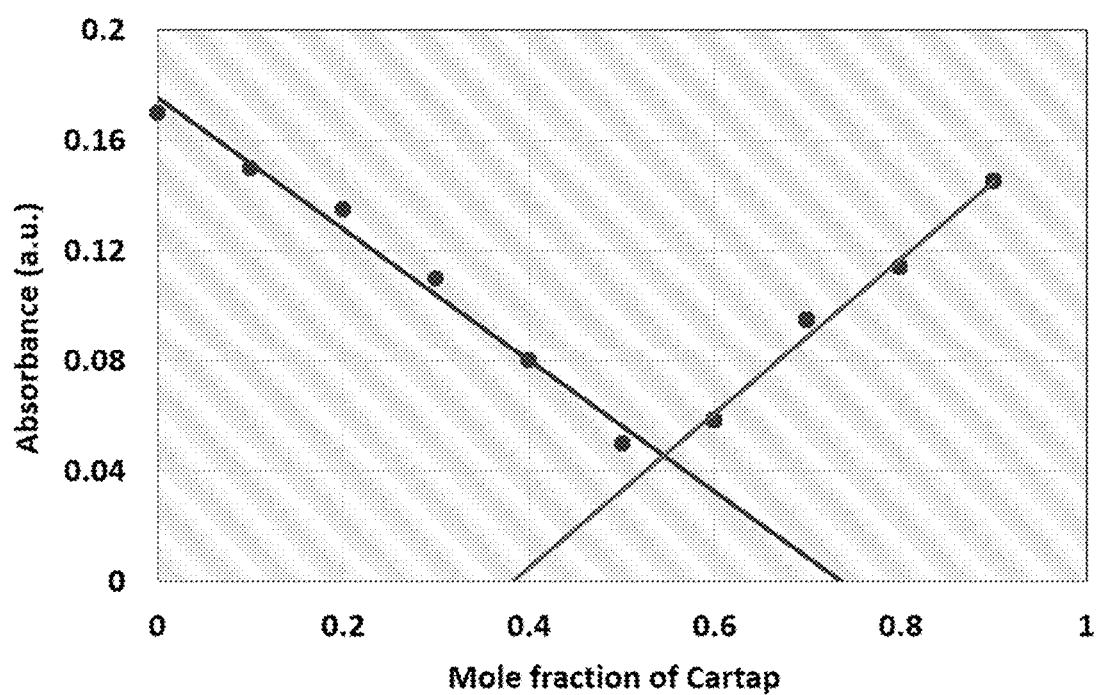
FIG. 14 depicts a job plot for binding ratio.
Figure 15:
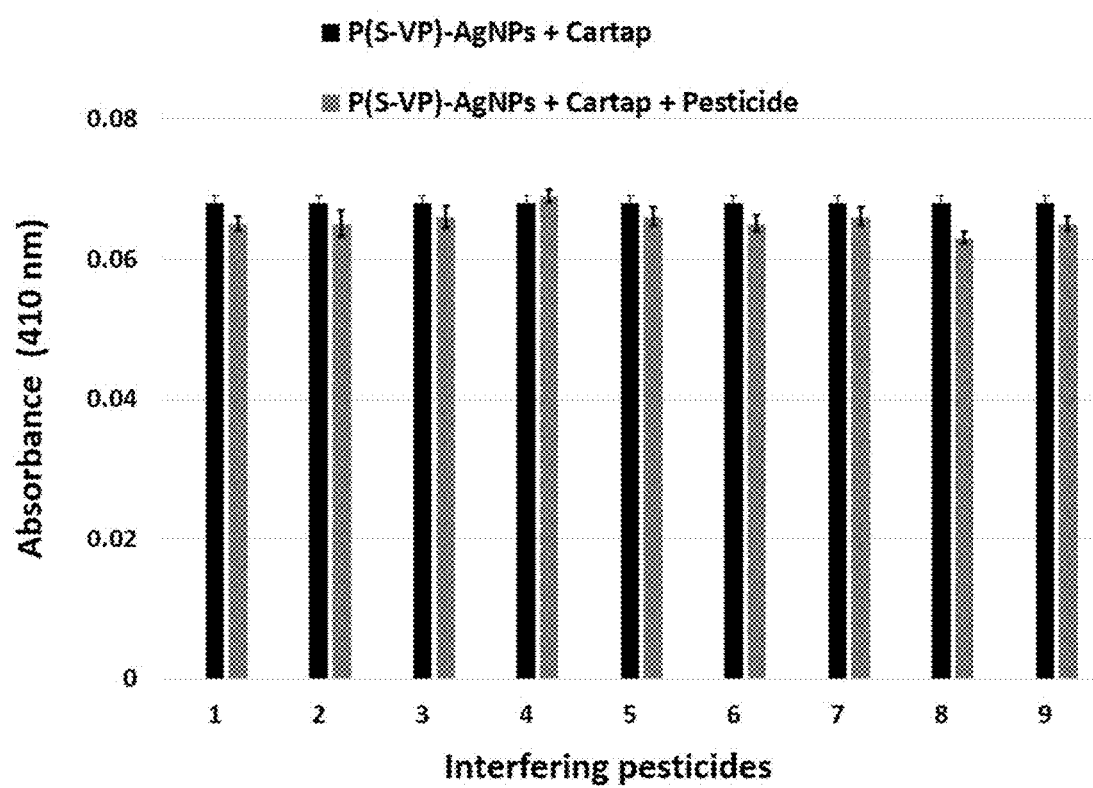
FIG. 15 depicts the effect of interfering insecticides on cartap detection by P(S-VP)-AgNPs, 1: deltamethrin, 2: Alpha-cypermethrin, 3: carbofuran, 4: chlorfenapyr, 5: Lambda-cyhlalothrin, 6: diuron, 7: imidacloprid, 8: lufenron, 9: clodinafop propargyl.

A solution obtained by diluting the thiocarbamate insecticide cartap to a concentration of 0.1 mM and P(S-VP)-AgNPs (Example 4) were mixed in different volume ratios but keeping the final volume constant and the mixture was allowed to react at room temperature. Thereafter, the absorption spectrum of the mixture was measured using UV-visible spectrophotometer. The absorption data was plotted by job's method, FIG. 14. The job plot indicated that the binding stoichiometry between P(S-VP)-AgNPs and cartap was 1:1.

Example 13

Effect of Interference of Other Competing Insecticides on Cartap Detection

A solution obtained by diluting the thiocarbamate insecticide cartap to a concentration of 0.1 mM (Example 4), P(S-VP)-AgNPs and solution of each interfering insecticide (0.1 mM) including; deltamethrin, Alpha-cypermethrin, carbofuran, chlorfenapyr, Lambda-cyhlalothrin, diuron, imidacloprid, lufenron and clodinafop propargyl were mixed at a volume ratio of 1:1:1. The mixture was allowed to react at room temperature for a while and the absorption spectrum of the mixture was measured.

All the mixtures possessed a shift in the absorption spectrum as other insecticide is not present. Practical demand of chemosensor for any application is its specificity for the analyte in presence of other interferents. It is noticed that the addition of nine different interfering insecticides in similar quantity does not have any pronounced effect on cartap recognition, FIG. 14.

Example 14

Comparison of Current Invention with Other Cartap Detection Methods

The comparison of reported detection methods for cartap by different techniques with current study is presented in TABLE 1. As can be noticed, the limit of detection of instrumental methods for determination of cartap is lower. However, the cartap recognition system proposed in current invention offers several advantages such as facile and fast synthesis of P(S-VP)-AgNPs, short detection time, low detection limit, low analysis cost, no requirement of sample pre-treatment etc. Hence, the proposed method approaches a striking platform for the conceivable practical applications in alarm system for determination of cartap. The limit of detection and detectable range of the cartap covers practically important range. The invented sensor is low cost, requires no advanced instrumentation can be employed for routine analysis.

| Methods/ Materials | Analytical ranges | LoD | Interfering species | Sample | Comments |
| --- | --- | --- | --- | --- | --- |
| HPLC | 50-400 pmol | 10 pmol | — | Water | specific electrochemical detector is required |
| GC-MS | 0.05-5.0 µgL$^{-1}$ | 10 µg L$^{-1}$ | Cartap metabolites | Human serum | Expensive instrumentation |
| Flourescence/ CB[7]-PAL | 0.009-2.4 µgmL$^{-1}$ | 0.0029 µgmL$^{-1}$ | Thiram, daminozide, promethazine hydrochloride, diphenhydramine hydrochloride, chlorphenamine, maleate | Grain, vegetable | Expensive instrumentation, tedious extraction procedure |
| Flourescence/ AuNPs-CdTe QDs | 0.01-0.50 mgkg$^{-1}$ | 8.24 mgkg$^{-1}$ | Methamidophos, imidacloprid, methomyl, carbaryl, acetamiprid | Chinese cabbage | Expensive instrumentation, tedious pre-treatment procedure |
| Photoluminescene/ Au@Ag nanoparticles | 0.222-0.709 mgkg$^{-1}$ | 0.0062 mgkg$^{-1}$ | Ometholate, aldicarb, amitraz, dichlorovos, methamidophos, imidacloprid, triazophos, methomyl, carbaryl, acetamiprid | — | Expensive instrument, pre-treatment, time consuming |
| Colorimetry/ Au NPs | 50-250 µgkg$^{-1}$ | 40 µgkg$^{-1}$ | Ometholate, aldicarb, amitraz, dichlorovos, methamidophos, imidacloprid, triazophos, methomyl, carbaryl | Tea, kiwifruit, rice, cabbage | low cost, tedious pre-treatment procedure |
| Colorimetry/ Au NPs | 0.05-0.6 mgkg$^{-1}$ | 0.04 mgkg$^{-1}$ | Ometholate, aldicarb, amitraz, dichlorvos, methamidophos, imidacloprid, triazophos, methomyl, carbaryl, acetamiprid | Cabbage, tea | low cost, tedious pre-treatment procedure |
| Colorimetry/ Ag NPs | 0.036-0.36 µgL$^{-1}$ | 0.06 µgL$^{-1}$ | Deltamethrin, Alpha-cypermethrin, carbofuran, chlorfenapyr, Lambda-cyhlalothrin, diuron, imidacloprid, lufenron, clodinafop propargyl. | Water, blood plasma | Easy synthesis compared to AuNPs, low cost, more sensitive, No pre-treatment of sample |

Example 15

Detection and Quantification of Cartap in Spiked Water and Human Blood Plasma Using Embodiments of the Present Invention The detection and quantification of cartap in spiked tap water, surface runoff water and blood plasma was conducted by allowing P(S-VP)-AgNPs to react with cartap and measuring the absorption spectrum using UV-visible spectrophotometer (the concentration and mixing ratio were the same as described in Example 4).

15.1. Detection and Quantification of Cartap in Spiked Tap Water

Figure 16A:
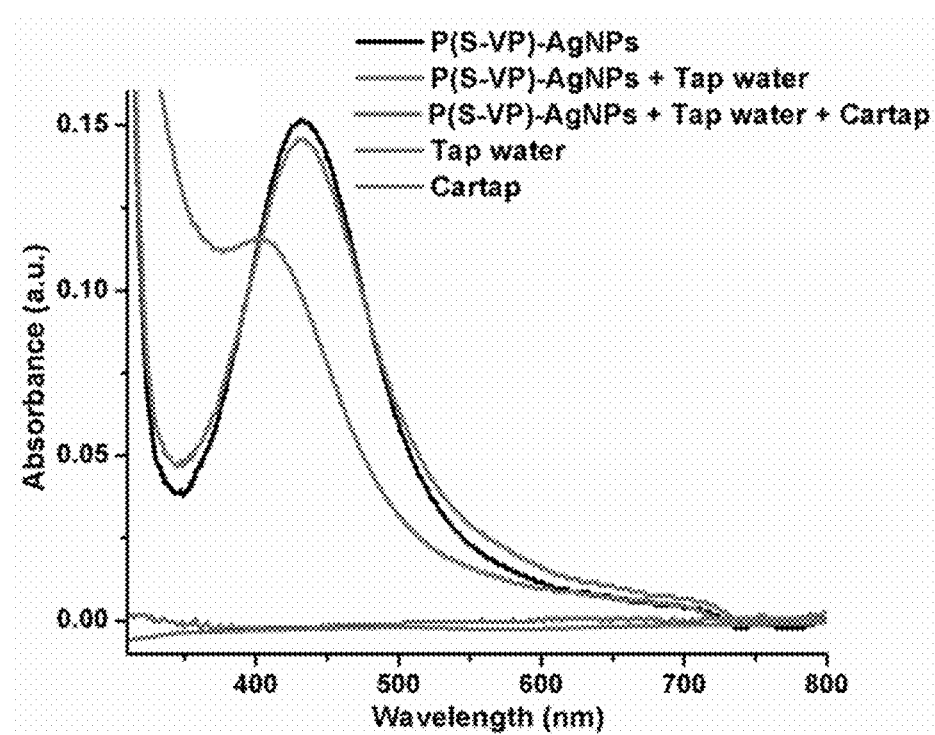
FIG. 16A depicts the effect of cartap on absorbance intensity of P(S-VP)-AgNPs in tap water.

A 0.1 mM solution of thiocarbamate insecticide cartap was prepared in 4.0 mL of tap water and diluted with 6.0 mL of methanol. P(S-VP)-AgNPs and diluted tap water solution of cartap were mixed in equal volume ratios. The mixture was allowed to react at room temperature and its absorption spectrum was measured. A distinct cartap recognition signal is observed in P(S-VP)-AgNPs with 0.1 mM cartap spiked tap water, FIG. 16A.

15.2. Detection and Quantification of Cartap in Spiked Surface Runoff Water

Figure 16B:
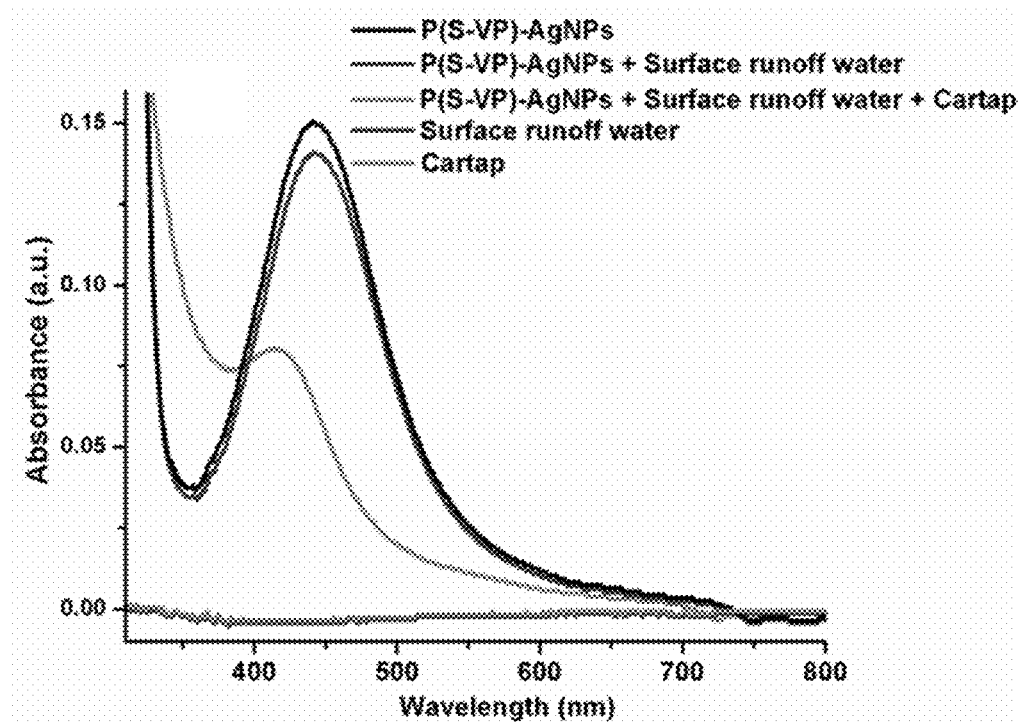
FIG. 16B depicts the effect of cartap on absorbance intensity of P(S-VP)-AgNPs in surface runoff water.

A 0.1 mM solution of thiocarbamate insecticide cartap was prepared in 4.0 mL of surface runoff water and diluted with 6.0 mL of methanol. P(S-VP)-AgNPs and diluted tap water solution of cartap were mixed in equal volume ratios. The mixture was allowed to react at room temperature and its absorption spectrum was measured. A distinct cartap recognition signal is observed in P(S-VP)-AgNPs with 0.1 mM cartap spiked surface runoff water, FIG. 16B.

15.3. Detection and Quantification of Cartap in Spiked Human Blood Plasma

Figure 16C:
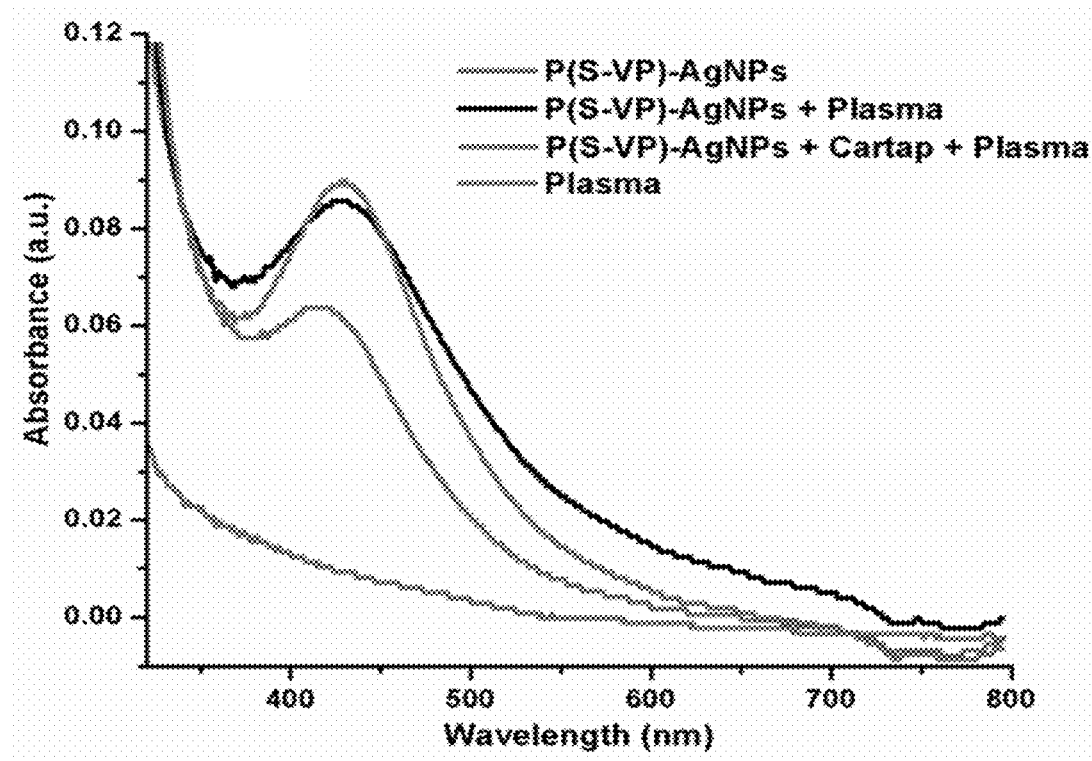
FIG. 16C depicts the effect of cartap on absorbance intensity of P(S-VP)-AgNPs in human blood plasma.

Two different stock solutions were prepared taking 1.0 mL of plasma and 2.0 mL of P(S-VP)-AgNPs, diluted with methanol up to 5 milliliter. 1.0 mL of plasma containing AgNPs stock solution was analyzed without adding cartap while the other solution was spiked with 1.0 mL of 0.1 mM cartap solution. Only a hypochromic shift with a slight blue shift of 4-5 nm band is observed for cartap in spiked human blood plasma, FIG. 16C.

What is claimed is:

1. A spectrophotometric method for quantification of cartap, a thiocarbamate insecticide comprising measuring a shift in ultraviolet-visible spectra, from 428 nm to 410 nm, of a polystyrene-block-poly(2-vinylpyridine)-conjugated silver nanoparticles [P(S-VP)-AgNPs] when combined with cartap in a 1:1 molar ratio in an aqueous solution.

2. The spectrophotometric method of claim 1, wherein P(S-VP)-AgNPs comprise about 80 weight % of P(S-VP).

3. The spectrophotometric method of claim 1, wherein the aqueous solution has a pH ranging between range of 7-12, preferable 8-10.

4. The spectrophotometric method of claim 1, wherein P(S-VP)-AgNPs have a mean diameter ranging between 100-110 nm.

5. The method of claim 1, wherein the cartap quantification detection sensitivity is at least 0.1 mM.

6. The method of claim 1, wherein the cartap detection method is applicable to complex matrices such as tap water, surface run-off water, human blood plasma in presence of other interfering species.

* * * * *